(12) United States Patent  (10) Patent No.: US 8,764,825 B2
Ledergerber  (45) Date of Patent: *Jul. 1, 2014

(54) GEL-SIMULATING AND MODULATING BUTTRESS PROSTHESIS

(71) Applicant: Walter J. Ledergerber, Dublin, CA (US)

(72) Inventor: Walter J. Ledergerber, Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/952,194

(22) Filed: Jul. 26, 2013

(65) Prior Publication Data

US 2013/0317610 A1 Nov. 28, 2013

Related U.S. Application Data

(63) Continuation-in-part of application No. 13/523,017, filed on Jun. 14, 2012, which is a continuation-in-part of application No. 12/360,979, filed on Jan. 28, 2009, now Pat. No. 8,202,316.

(60) Provisional application No. 61/024,405, filed on Jan. 29, 2008.

(51) Int. Cl.
*A61F 2/12* (2006.01)

(52) U.S. Cl.
USPC ............................................................ 623/8

(58) Field of Classification Search
USPC ........................................................ 623/7–8
See application file for complete search history.

(56) References Cited

U.S. PATENT DOCUMENTS

| | | | |
|---|---|---|---|
| 4,264,990 A * | 5/1981 | Hamas | 623/8 |
| 8,556,968 B2 * | 10/2013 | Hamas et al. | 623/8 |
| 2009/0270985 A1 * | 10/2009 | Schuessler | 623/8 |
| 2010/0114311 A1 * | 5/2010 | Becker | 623/8 |
| 2012/0053690 A1 * | 3/2012 | Frank | 623/8 |
| 2012/0078366 A1 * | 3/2012 | Jones et al. | 623/8 |
| 2012/0253460 A1 * | 10/2012 | Ledergerber | 623/8 |
| 2013/0131800 A1 * | 5/2013 | Schuessler | 623/8 |

* cited by examiner

*Primary Examiner* — Suzette J Gherbi
(74) *Attorney, Agent, or Firm* — David B. Murphy; O'Melveny & Myers LLP

(57) ABSTRACT

An implantable mammary prosthesis includes an urchin buttress fill port structure. The fill port structure preferably comprises a shell, the shell including an opening, a compartment interior to the shell adapted to contain a filler. The urchin buttress is generally cup-shaped, and is disposed within the shell. The urchin buttress is preferably attached to the shell adjacent the opening to form a fluidic seal, optionally via a sealing flange. The urchin buttress may include one or more ribs, such as to provide structural support to the urchin buttress. Preferably, a reservoir is disposed external to the shell.

30 Claims, 14 Drawing Sheets

GEL-SIMULATING AND MODULATING BUTTRESS PROSTHESIS

PRIORITY CLAIM

This application is a continuation-in-part application of U.S. Utility application Ser. No. 13/523,017, entitled "Modulating Buttress Saline Mammary Prosthesis", filed Jun. 14, 2012, published as US Patent Application Publication US 2012/0253460 on Oct. 4, 2012, which is a continuation-in-part application of U.S. Utility application Ser. No. 12/360,979, entitled "Modulating Buttress Saline Mammary Prosthesis", filed Jan. 28, 2009, issued as U.S. Pat. No. 8,202,316 on Jun. 19, 2012, which application claims the benefit of and priority to U.S. Provisional patent application Ser. No. 61/024,405, entitled "Modulating Buttress Saline Mammary Prosthesis Gel Simulating Saline Implant", filed Jan. 29, 2008, all hereby incorporated by reference as if fully set forth herein.

FIELD OF INVENTION

This invention relates to implantable prosthetic devices and to tissue expanders used in plastic and reconstructive surgery used to stretch tissues. More particularly, the invention relates generally to a preferably saline, or slurry, or both, implant that simulates the properties of gel implants.

BACKGROUND OF THE INVENTION

Most tissue expanders and soft tissue-simulating implantable prostheses have been utilized to enhance or reconstruct the female breast. While success has been achieved across the spectrum of devices and procedures, the predictability of success has very often been a matter of intelligent guesswork by implanting surgeons. Despite the sometimes fortuitous selection of patients with low allergic response to polysiloxane implant fillers, the search for a broadly acceptable implant configuration has been protracted by differing implant shell and surface topographies, and by the range of quality of surgical outcomes. Silicone gel-filled implants, having the seductive ex vivo visual and tactile characteristics of clear transparency and gel consistency, have driven the "criteria" for such an implant rather than has the clinically more beneficial criterion of non-antigenicity.

Ultimately, it has become clear that silicone oils originating inside a gel-filled implant could manifest on the exterior surface of the shell, and being antigenic, could stimulate a self-protective response on the part of the patient. As a consequence, very dense tough scar tissue forms which serves to deform and severely harden what would otherwise be a soft breast. Such failures have stimulated a wider search for possible solutions including changes in surgical technique such as placing the implant, usually gel-filled silicone, into the sub-pectoral position. Sub-muscular placement of implants has increased the complication rate.

Complex multi-component implant constructions including textured shells, "protective" saline compartmentalization around silicone gel compartments, and baffling schemes and others have been tried and eventually rejected as being problematic for a variety of reasons. Likewise, triglyceride fillers and others have met similar fates.

Various other topologies, coverings and texturizing methods and structures have been contributed to the art. See for example my earlier U.S. Pat. No. 4,955,907 entitled "Implantable Prosthetic Device", and U.S. Pat. No. 6,228,116 entitled "Tissue Expander". Those patents are hereby incorporated by reference as if fully set forth herein.

FIG. 1 is a vertical cross-section of a prior art multi-compartment saline implant, specifically FIG. 21 from my U.S. Pat. No. 5,282,856. It illustrates a sessile normal saline-filled compartment adherent to the internal base of the implant surrounded and in contact with the contents of the surrounding volume, here a sponge. FIG. 2 is a vertical cross-section of a prior art saline implant, specifically FIG. 23 from my U.S. Pat. No. 5,282,856, whose entire volume is occupied by spheres of different diameters. My U.S. Pat. No. 5,282,856 is hereby incorporated by reference as if fully set forth herein, with the identified figures being specifically incorporated by reference as if fully set forth herein.

Yet, a safer natural alternative, the saline-filled implant has always been available. Unfortunately, resistance to its broad adoption has been based on esthetic consideration both ex vivo and as implanted. Its acceptance has been limited by its less than satisfactory "off-clear" appearance, the propensity to wrinkle due to a stiff high density shell and the fact that normal saline filler itself offers little resistance to deformation and is too quick to propagate visible waves on deformation. Such features have often led to embarrassment for the patient. Thus, there is an ongoing need for an enhanced performance saline implant which simulates the tactile features and performance of a silicone elastomer gel-filled implant but which lacks the antigenicity of filler silicone oils.

SUMMARY OF INVENTION

In one aspect, an implantable mammary prosthesis includes a shell and an urchin buttress. The shell includes an opening and defines a compartment interior to the shell adapted to contain a filler, such as saline or a slurry. An urchin buttress is disposed within the shell, the urchin buttress being preferably urchin or cup shaped and being disposed within the shell. The urchin buttress is attached to the shell via a flange oriented toward the center of the implant adjacent the opening to form a fluidic seal. Preferably, a spring, such as a coil spring, is disposed within the urchin buttress to aid in maintaining the shape of the buttress after undergoing deformation or otherwise being subject to a force to provide a counterforce to deformation of the buttress. In one implementation, a reservoir is disposed external to the shell.

In yet another aspect of the invention, one or more fill ports may be utilized, such as in the use of a dedicated slurry fill port to fill the compartment defined by the interior of the shell and the exterior of the urchin. Fill ports directly connected to the shell may be utilized, being particularly adapted for input of slurry or saline, depending upon the intended filling for the implant. The fill port is preferably resealable, such as by providing two adjacent lips, which are closed together in the sealed configuration, and pursed or slightly opened when in the implant is being filled.

In yet another aspect, an implantable prosthesis is provided having a shell and an interior buttress. The shell includes an opening adapted to receive the buttress, the interior of the shell and exterior of the buttress defining an interior compartment adapted to contain a filler, such as saline or a slurry. The buttress includes a sealing portion which attaches to the interior of the shell to form a fluidic seal. The sealing portion may comprise a flange, which may be disposed toward the interior of the implant in an urchin configuration or may be disposed away from the interior of the implant in a limpet configuration. The buttress includes one or more deformation compensating structures, such as ribs and or springs. A membrane is disposed adjacent to the buttress so as to define a second fluid compartment with the interior of the buttress. Preferably, a reservoir is provided external to the buttress, and is in fluid communication with the second fluid compartment.

An implantable mammary prosthesis includes an urchin buttress fill port structure. The fill port structure preferably comprises a shell, the shell including an opening, a compartment interior to the shell adapted to contain a filler. The urchin buttress is generally cup-shaped, and is disposed within the shell. The urchin buttress is preferably attached to the shell adjacent the opening to form a fluidic seal, optionally via a sealing flange. The urchin buttress may include one or more ribs, such as to provide structural support to the urchin buttress. In yet another aspect, an enhanced implantable mammary prosthesis comprises a shell and a slurry filler compartment interior to the shell containing slurry filler. A fluid compartment is in pressure transmissive contact with the slurry filler. The fluid compartment is deformable from a neutral profile under pressure from the slurry filler, and it recoils to the neutral profile when not under pressure. A reservoir is disposed preferably external to the shell. The reservoir and the fluid compartment are fluidically coupled by a port. A limiting membrane region is disposed between the fluid compartment and the reservoir to provide sufficient structural rigidity so that the pressure transmission from the slurry filler can be effectively transmitted to the fluid compartment and in turn can be relieved by expansion of the reservoir by fluid passing from the fluid space through the port. Optionally, additional structures may be provided on or in the fluid compartment to aid in the recoil of the fluid compartment.

In yet another aspect, the combination of components including 1) a silicone elastomer shell which is compliant to the touch, but highly resistant to rupture due to abrasion and also resistant to the transudation of water-consistency diluents, 2) a slurry filler consisting of a biocompatible fluid, such as normal saline, and dense suspension preferably comprising a prodigious number of medical glass or biocompatible polymer micro-toroids or spheres, 3) a structure or buttress preferably comprising a sessile hollow silicone elastomer structure or buttress situated within and adhesively attached internal to the shell at the base, and 4) a lens-like reservoir being located external to the implant but in fluid communication with the structure or buttress which is located internal to the shell, with a thick limiting membrane interposed between the fluid compartment and the reservoir. The buttress preferably contains a buffered biocompatible fluid, such as normal saline, which is voided to the lens-like reservoir in order to accommodate deformation of the buttress under the influence of increased pressure in the slurry compartment. As pressure in the slurry compartment again decreases, the buttress assumes its original profile (rebounds) due to its relative stiffness and recoil, with the fluid in the reservoir being sucked back into the buttress.

The enhanced-performance slurry of the invention has increased viscosity due to the large number of individual particles within it in frictional interference with other like particles and the ratio of solid to liquid components. Buffered normal saline is the preferred fluid. The "solid-particulate" component ideally is comprised of a prodigious number of "closest-packing" diameters of medical glass spheres or biocompatible polymer spheres or micro-toroids which may be textured or metal-plated to enhance their performance. Besides frictional interference, electrostatic forces and surface tension influence overall viscosity. Amorphous glass "fit" can be admixed to increase friction, as well. Silver plated glass particles will additionally confer bacteriostatic properties to such a slurry. The slurry will have an ideal viscosity when it resembles that of toothpaste or thin bread dough.

DETAILED DESCRIPTION OF THE INVENTION

The attached figures serve to illustrate the general and preferred embodiments of the invention.

Figure 1:
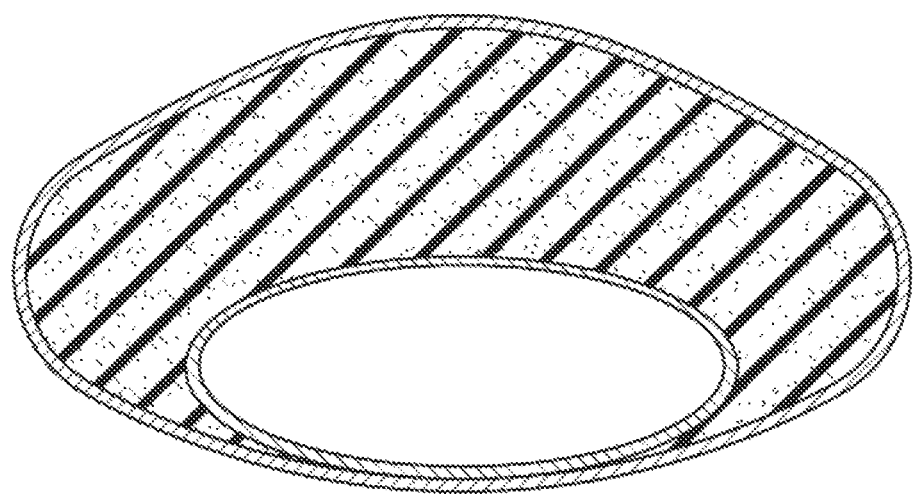
FIG. 1 is a vertical cross-section of a prior art multi-compartment saline implant, specifically FIG. 21 from my U.S. Pat. No. 5,282,856.
Figure 2:
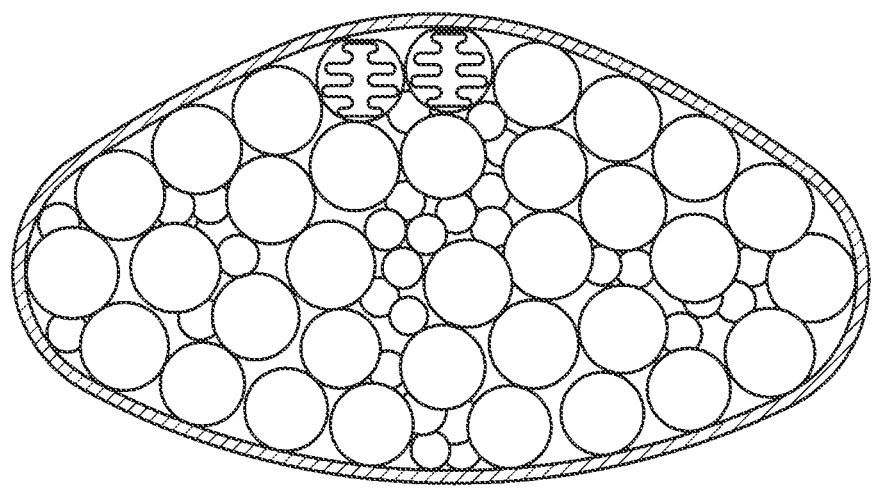
FIG. 2 is a vertical cross-section of a prior art saline implant, specifically FIG. 23 from my U.S. Pat. No. 5,282,856.
Figure 3A:
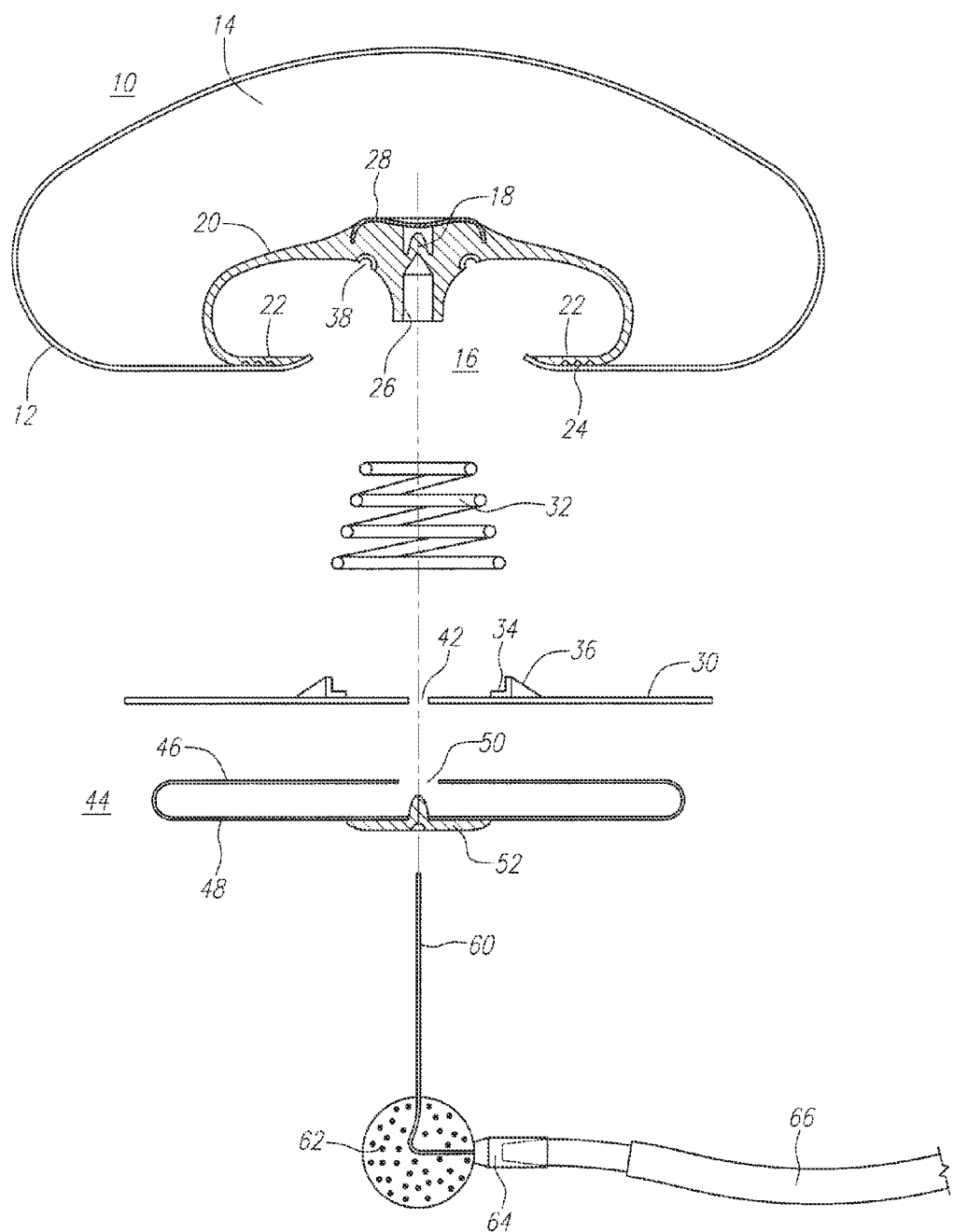
FIGS. 3A and 3B are exploded and as assembled cross-sectional drawings, respectively, of an urchin buttress implant.
Figure 3B:
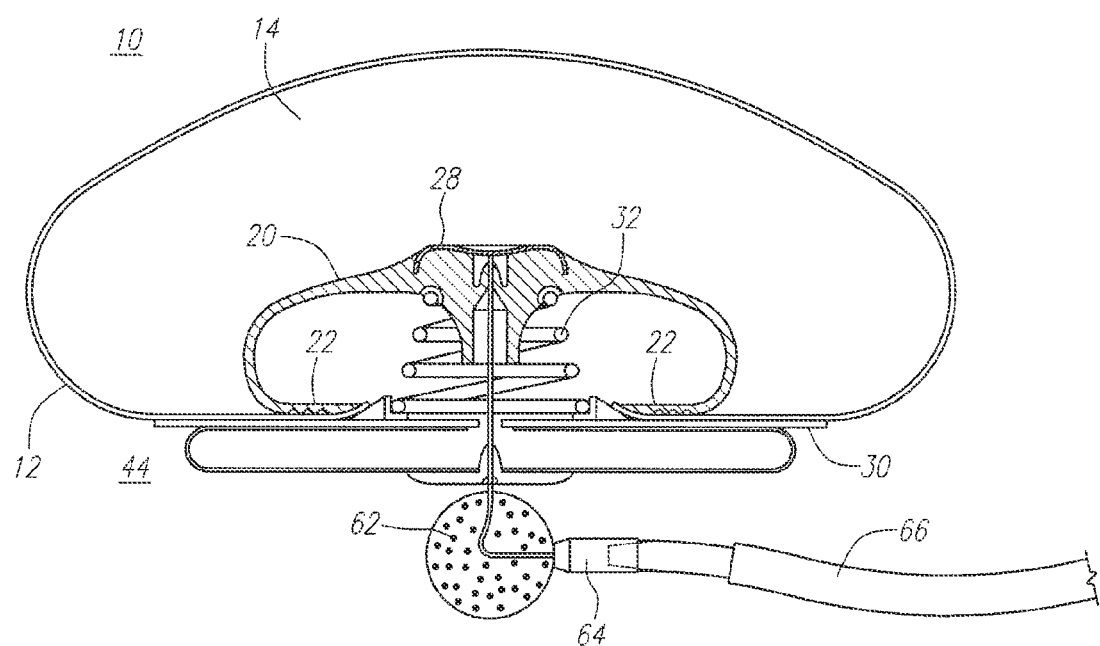

FIGS. 3A and 3B are exploded and as assembled cross-sectional drawings, respectively, of an urchin buttress implant. While the urchin buttress implant may be used with the structures described herein, it may be utilized on its own without incorporation of those features. In one embodiment, the urchin buttress implant is a normal saline implant, or a slurry implant, or a combination of the two.

The implant 10 includes a shell 12, which may be a single layer or multi-layer shell, defining a volume or chamber 14 in which a filler material, such as normal saline or slurry, resides in the final assembled device after implantation. A shell opening 16 provides access for the urchin buttress 20. The urchin buttress 20 may be shaped as an urchin, as shown, or may alternately include small bellows. The implant 10 preferably includes a superior pole portion. The shell includes an interior portion and an exterior portion, the exterior of the shell may be smooth or textured. The urchin buttress 20 is preferably semi-spherical or otherwise cup-shaped. A flange 22 is disposed at the periphery of the urchin buttress 20, and preferably provides a surface, such as adhesive flow ridges 24, adapted for sealing the overall urchin to the shell 12. Optional adhesive flow ridges, such as approximately 0.05 inches wide, may be disposed on the bottom surface of the sealing flange 22.

The flange 22 in FIGS. 3A and 3B extend inward toward the center of the implant. The side wall portions of the urchin buttress 20 may be more rounded and the curved side portion accommodates the inward disposed flange 22 in FIGS. 3A and 3B (as compared to FIGS. 5A, 5B, 6A and 6B). The rounded and curved side portion advantageously responds to pressure from the chamber 14 and avoids sharp creasing of the body of the urchin, reducing the instance of creasing, folding and/or tearing. Additionally, during accommodation to increased pressure, the urchin buttress can respond to very small increments in pressure in a smooth way. This feature allows for finer gradations of structure and scalability. Further, there is a decreased likelihood of de-lamination because the shell reaches onto the curb internally and is adhered to it. The flange 22 in FIGS. 5A and 5B extends outward away from the center of the implant.

In one implementation, a spring 32 provides support for the buttress in order to compensate for or provide a counter force to compression of the buttress. The spring may be of any form consistent with the goals of the device, such as a coil spring, and more particularly a coil spring having a wider diameter at the base as compared to the top. The top portion of the spring may contact the inner side of the urchin buttress 20. A grommet 38, such as one disposed within a groove, or indented surface may be formed on the inner surface of the buttress 20 to provide for positional placement of the spring. The base of the spring may optionally rest adjacent a grommet 34, preferably a circular shaped grommet. An abutting curb 36 may be provided, and preferably includes a sloped portion to provide additional structural support at the end of the flange 22 and the end of the shell 12.

The buttress 20 optionally includes an internal guide surface (as for use in filling, as described, below). A sealable valve 18 provides for the interface with the larger implant volume 14. Preferably, a screen 28 is provided above the guide surface to prevent penetration of a fill tool, such as cannula 60, into the larger implant volume 14. The screen 28 preferably includes fenestrations generally sized to be smaller than the diameter of the fill tool. It may further be concave to aid the surgeon in orientation and placement.

A basilar membrane 30, single or multi-layer, optionally reinforced, e.g., with Kevlar®, Nylon® or carbon fiber, is provided with a fluid gate 32 disposed generally in the center of the basilar membrane 30. A lenticular reservoir 44 preferably includes a first surface 46 including a fluid gate 50. The first surface 46 supports adhesive, such as UV curable silicon adhesive, or any adhesive or coupling equivalent, during the assembly process, discussed in more detail, below. The second surface 48 couples with an access port 52, preferably a self-sealing access port, optionally having a depressed indentation to aid in locating the center of the access port 52. Optionally, an arrestor plug, such as in a biscuit or spherical shape, allows the free passage of water consistency fillers. The plug is preferably made of ceramic or sintered glass beads.

Figure 4A:
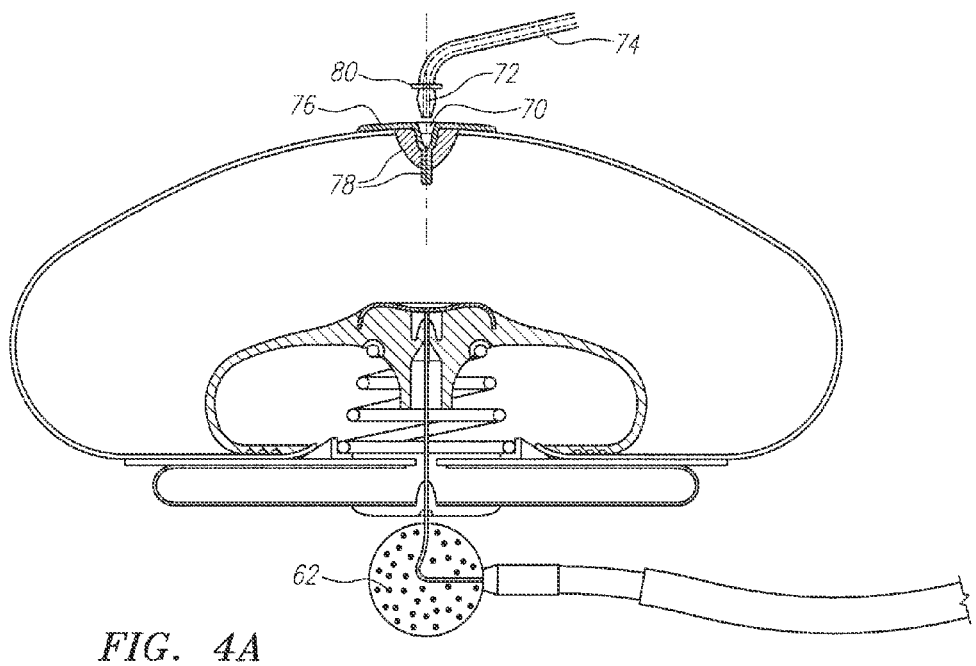
FIGS. 4A and 4B are cross-sectional drawings of fill port structures advantageously used with a slurry filling and a saline filling, respectively, for the various implants.
Figure 4B:
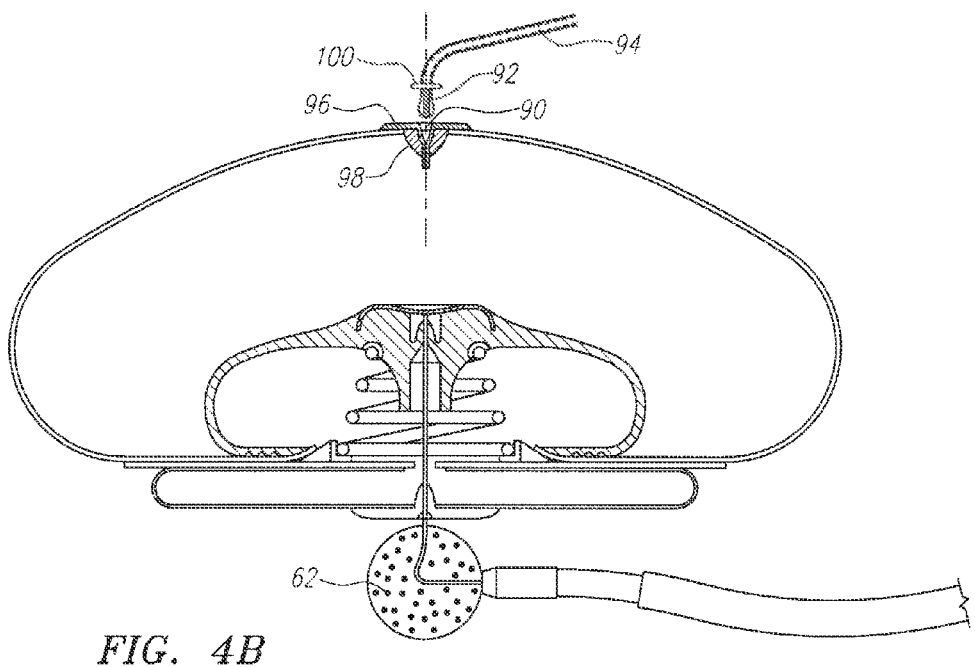

With reference to FIGS. 4A and 4B, fill ports may be provided, in addition to or in lieu of the sealable valve shown in FIGS. 3A and 3B and FIGS. 5A and 5B. FIG. 4A shows a fill port adapted to fill the volume 14 with slurry (assuming the implant is not completely saline filled). While shown at the apical polar position, the fill port may be located elsewhere on the shell 12. A fill port 70 is adapted to sealingly mate with a coupler 72 of a slurry fill tube 74, which is in turn connected to a slurry source (not shown). An optional collar 80 serves for penetration arrest. The fill port 70 forms a depression on the surface of the overall implant 10. Resealable pursing lips 78 conduct the slurry from the slurry fill tube 74 to the inner volume 14 when the slurry is provided at a pressure which causes the lips 78 to purse or open slightly. When the slurry compartment is filled, and the slurry opening pressure is removed, the lips 78 return to a closed or sealed condition. Optionally, additional support struts or vanes may be added to the side of the pursing lips 78 to provide a closing force to aid in closure and to ensure a tight seal.

FIG. 4B shows a fill port adapted to fill the volume 14 with saline. While shown at the apical polar position, this fill port as well may be located elsewhere on the shell 12. A fill port 90 is adapted to sealingly mate with a coupler 92 of a saline fill probe 94, which is in turn connected to a saline source (not shown). An optional collar 96 serves for penetration arrest against arrestor plate 100. The fill port 90 forms a depression on the surface of the overall implant 10. Resealable pursing lips 98 conduct the saline from the saline fill probe 94 to the inner volume 14 when the saline is provided at a pressure which causes the lips 98 to purse or open slightly. When the saline is filled, and the saline pressure removed, the lips 98 return to a closed or sealed condition.

Figure 5A:
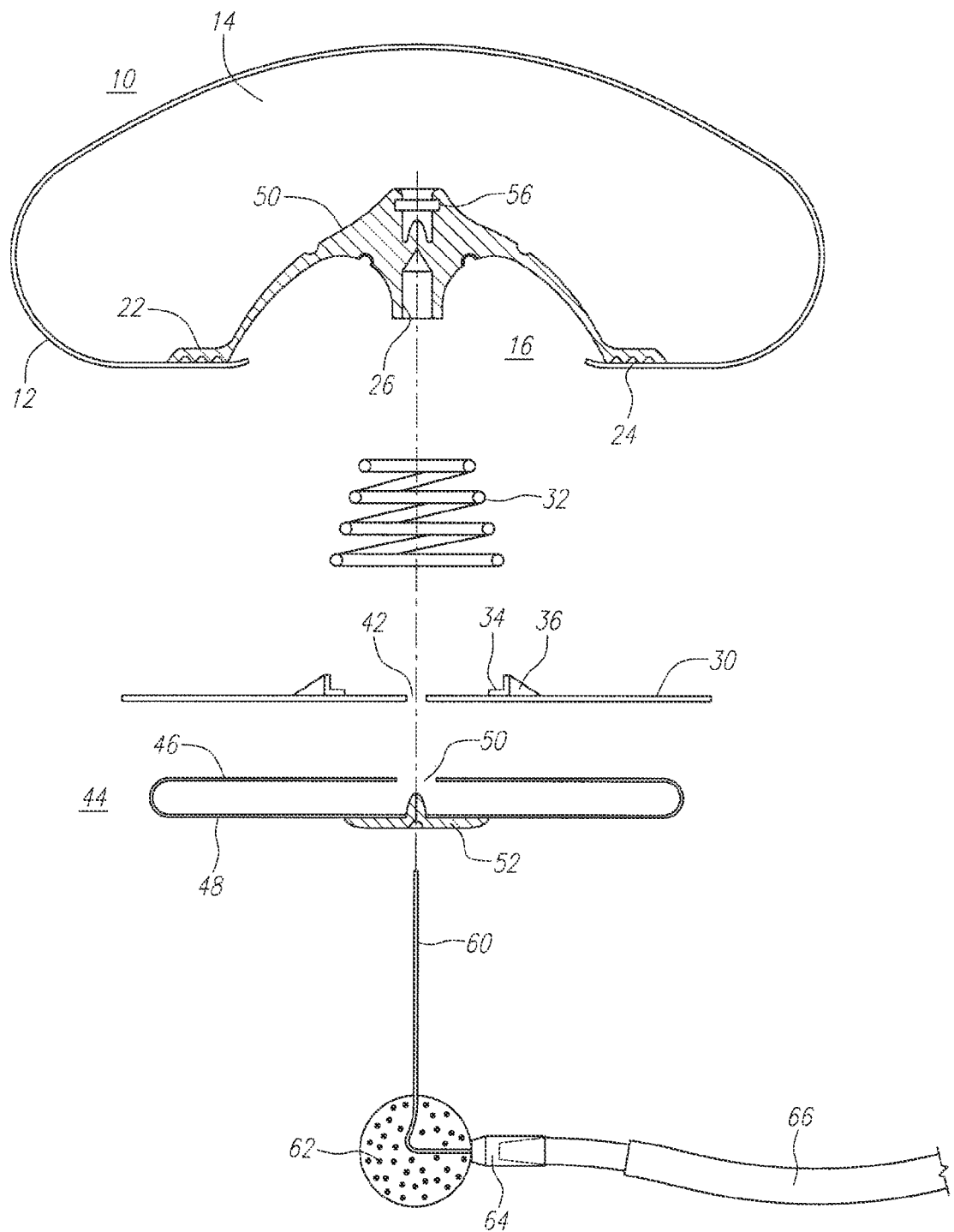
FIGS. 5A and 5B are exploded and as assembled cross-sectional drawings, respectively, of a spring containing limpet buttress implant.
Figure 5B:
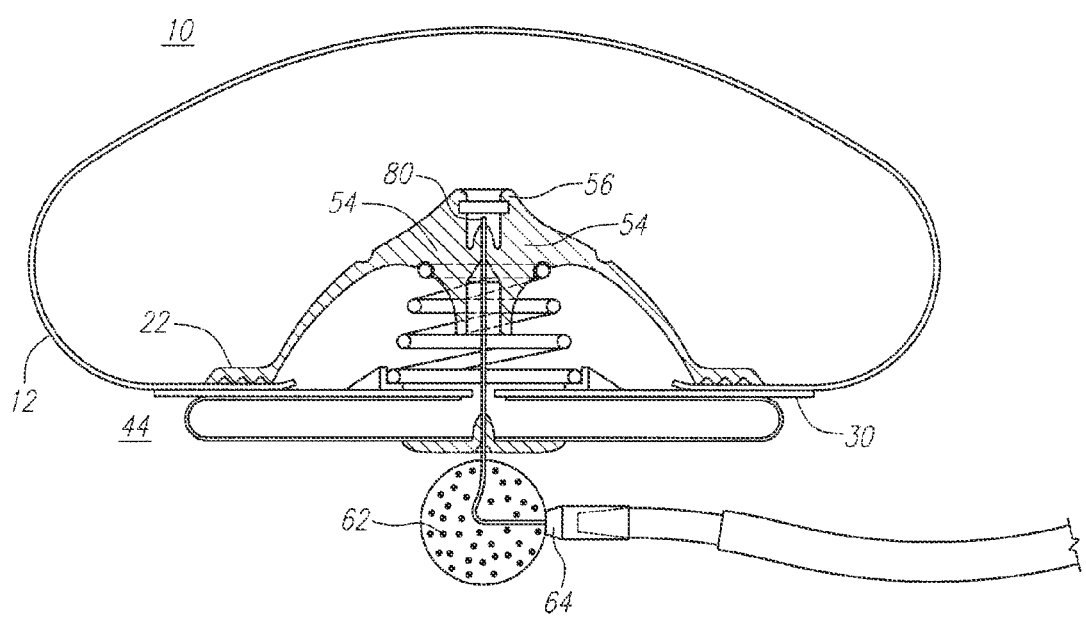

FIGS. 5A and 5B are exploded and assembled cross-sections, respectively, of a limpet buttress. FIGS. 5A and 5B have certain structural elements in common with FIGS. 3A and 3B, and will be similarly numbered when the same. The differences will be noted. The flange 22 in the limpet buttress is disposed outward from the center of the implant 10. FIGS. 5A and 5B are shown having a projecting portion 50 of the buttress. The structural shape and sizing of the projectile portion 50 may vary to provide structural support and aid in deformation restoration. An arrestor 56 may be included, such as a metal screen, so as to stop penetration of a filling device, such as cannula 60, during filling. The shell 12 includes an interior portion and an exterior portion, the exterior of the shell may be smooth or textured.

Figure 6A:
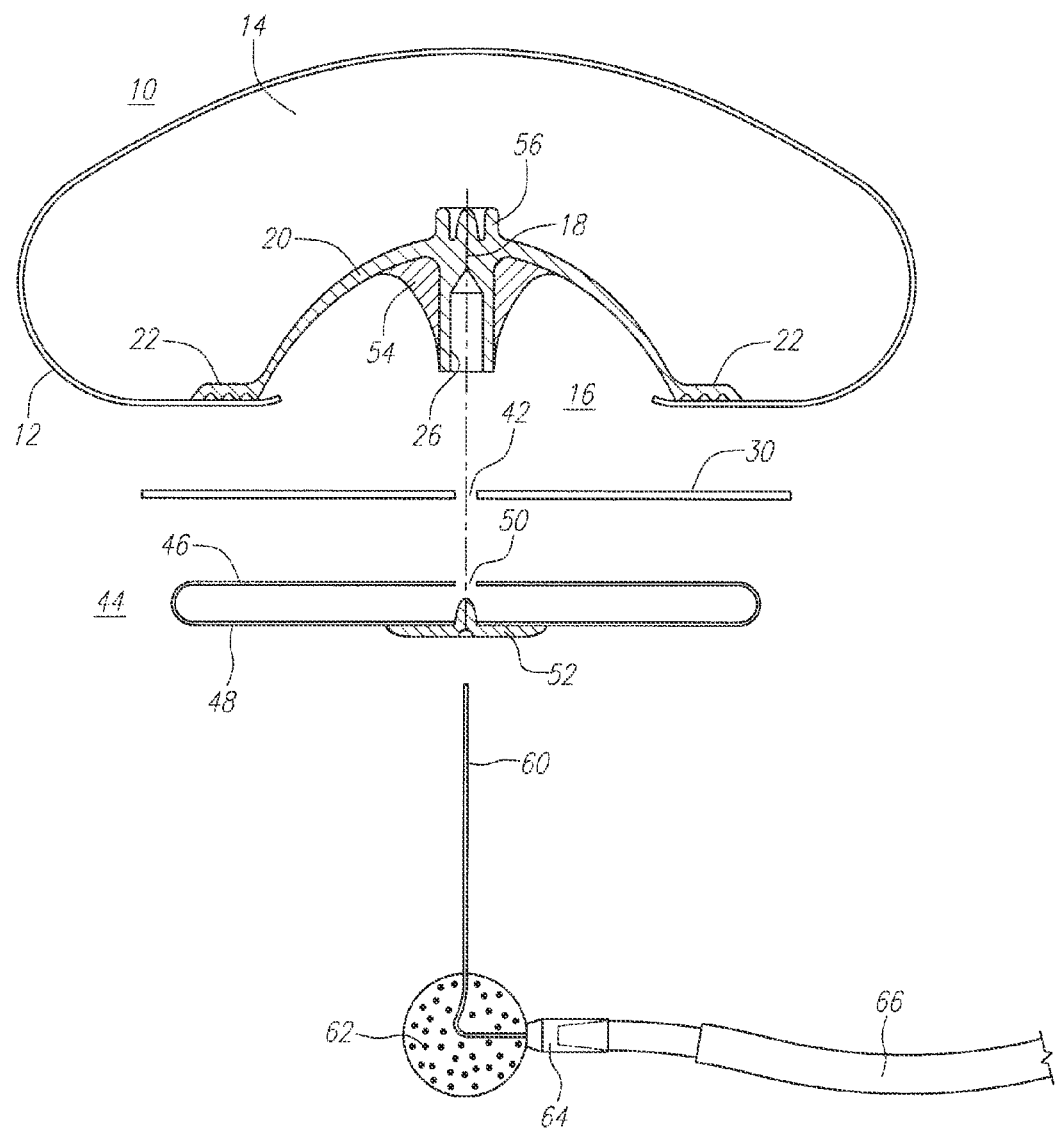
FIGS. 6A and 6B are exploded and as assembled cross-sectional drawings, respectively, of a limpet buttress implant without a spring.
Figure 6B:
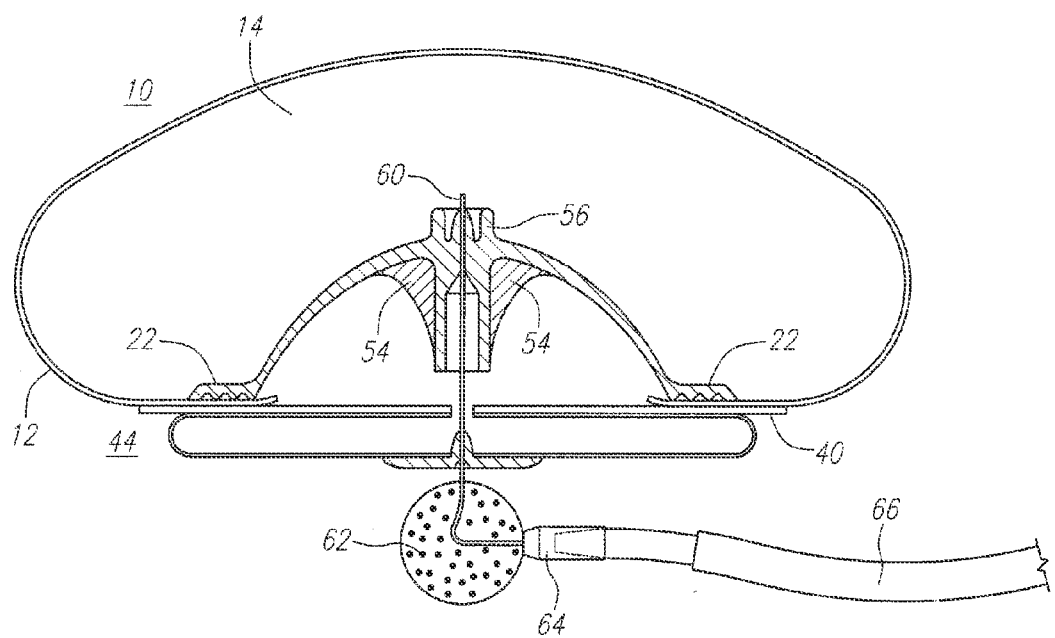

With reference to FIGS. 6A and 6B, one or more ribs 54, preferably four ribs 54 provide structural support and deformation restoral force for the limpet buttress 20. A ridge 56 may optionally be disposed at the superior pole of the limpet buttress 20. The ridge is preferably circular, and serves to provide protection for the shell 12, and advantageously may be used by the surgeon during implantation as a palpable orientation device. Preferably, an internal guide surface 58 is provided to assist in assembly. These structures may optionally be included in the other embodiments described herein. The shell includes an interior portion and an exterior portion, the exterior of the shell may be smooth or textured.

The various structures described may be selected so as to tune the overall feel and operation of the implant. In one goal, the implant will simulate a gel-filled implant. To achieve the desirable feel, numerous design choices may be made by those skilled in the art. The density of the slurry may be varied (either by the manufacturer, or optionally by the surgeon), such as by changing the ratio of particulates to diluents, etchings, silver plating of toroids, glass beads and 'frit'. The buttress 20 wall shape, material selection and thickness may be varied to achieve the desired feel and performance. The spring may be varied, such as in the number of coil turns, materials, thickness, and other factors to achieve the desired feel. The sizing of the fluidic interconnections 42, 50 may be selected to achieve the desired feel.

The implant 10 with the buttress feature may be assembled according to the following procedures. A shell 12 having an opening 16 is provided. The buttress is inserted into the shell 12 via the opening 16. Optionally, the combined structure may be inverted, and the buttress held by a tool contacting the internal guide surface. Adhesive is disposed on the sealing flange 22, preferably on the adhesive flow ridges 18, if present, and/or on the interior of the shell 12. The shell 12 and buttress are aligned and cured, such as by using UV light if the adhesive is UV curable. The spring is preferably positioned within the grommet or curb base on the basilar membrane 40. The basilar membrane 40 and the lenticular reservoir 44 are adhered to the buttress and shell combination. The fluid gate 42 should be aligned with the fluid gate 50. Optionally, air insufflation may be used to assist in the adhering procedures, such as by inflating one or more of the structures with air during the adhesion process. The preceding assembly steps need not be performed in any particular manner, so long as the overall assembled structure results.

The preferred methods of filling and implantation of the buttress implants, e.g., FIGS. 3A, 3B, 4A, 4B, 5A, 5B, 6A and 6B) is described. Preferably, all buttress implants are emplaced into the patient wound with the upper chamber 12 completely deflated and the buttress chamber filled with a specified amount of normal saline. All buttress implants are preferably placed into sub-glandular/supra-muscular plane.

Following are the preferred methods where normal saline is provided in the upper chamber 12 with filling being made via the cannula fill (not the additional saline port of FIG. 4B). With the implant outside patient, evacuate all air from the upper chamber via the cannula, such as a 20 gauge cannula, preferably having a blunt tip, serves to penetrate the access port 52 and then the buttress 20. The cannula should be long enough to deliver fluid into the volume 14, but preferably not so long as to risk penetration of the shell 12, such as at the superior pole of the implant. The cannula optionally passes through a grip 62, and couples to a fluid source (not shown). Any manner of connection to the fluid source may be used, such as via a Luer Lock, and tubing. The buttress and lenticular reservoir 44 may be angled relative to the chest in order to facilitate penetration of the cannula for filling. Optionally, arresting of the cannula penetration may be done via a cap, preferably made of stainless steel or polymeric material with fenestrations. Following is the preferred method: 1) insert cannula into dimple depression in base/insertion plate and using gentle technique, twistingly insert while holding textured grip while also grasping the ridge ring and base plate with the long finger and thumb of the opposite hand. 2) Remain spatially oriented and follow tactile clues for position of cannula tip inside the valve channel of the buttress. 3) Advance cannula tip until it "bottoms out" in the apex of the cone and valve channel, then advance through the cone, into and through the upper valve until the cannula makes palpable contact with the fenestrated arrestor cap, then stop. 4) Attach suction to cannula/stopcock combination and efficiently and completely evacuate all air from the upper chamber. 5) Pull cannula back into the lower valve channel. 6) Fill Buttress with normal saline, such as 20 ccs. 7) Remove residual air from the buttress by aspirating with syringe attached until the reservoir below the buttress contains the least amount of residual air possible. The Implant is now ready for installation.

Following is the preferred method of installation of the implant. 1) Place implant as previously prepared into the sub-glandular/supra-muscular pocket. 2) Re-insert the Cannula while stabilizing the Implant and tilting it 90 degrees with respect to the rib cage while grasping with the long finger over the ridge ring and thumb over the base/insertion plate, using the opposite hand. 3) Advance the cannula, carefully guiding it into the cone of the valve channel, and finally into the upper valve of the buttress, until it makes palpable contact with the fenestrated arrestor cap, then stop. 4) Add the prescribed amount of normal saline utilizing syringe pump method or gravity flow while stabilizing the cannula's position inside the buttress, then withdraw the cannula completely. 5) Adjust implant volume if necessary, using the afore-mentioned careful technique, keeping accurate record of changes. 6) Check implant performance check and position of implant.

Secondly, the following is the preferred method for filling and implanting the implant where a Normal Saline filler is used to fill in the upper chamber space 12. With implant outside patient, evacuate air from the upper chamber via the small silicone fill tube/nipple connector attached to the superior pole saline fillport and Operating Room suction attached to silicone fill tubing. The upper chamber should preferably be hyper-deflated to make insertion of the implant into the wound pocket as easy as possible. 2) Emplacement into the sub-glandular/supra-muscular wound pocket is now performed. 3) The fill tube/connector is reattached to the fill port, if necessary, and the prescribed amount of normal saline instilled by gravity flow. 4) When filling is complete, removal of the Nipple connector is easily accomplished by grasping it with a curved Kelly clamp. 5) The secure sealing plug with attached silicone band is placed into the depression. 6) implant performance check and standard wound closure techniques are utilized.

Third, the following is the preferred method for filling an implanting the implant where a slurry filling is used in the upper chamber space 12. 1) Place the implant as previously prepared into the sub-glandular/supra-muscular pocket. 2) Re-insert the slurry fill connector while stabilizing the implant and tilting it 90 degrees with respect to the rib cage while grasping the implant with the long finger over the ridge ring and thumb over the base/insertion plate, using the opposite hand. 3) Advance the head of the fill connector into the open cone of the valve until its progress is arrested by the arrestor plate behind the head, then stop. 4) Add the prescribed amount of slurry while stabilizing the fill connector's position outside the fill-port utilizing gravity or pump assisted fill method, then quickly withdraw the head when fill is complete. 5) Flush the fill-port with a generous amount (several cc's) of normal saline, then suction the area dry with O.R. suction. 6) Check the position of the implant and its performance as usual, then use usual wound suction and drainage technique, then close the wound in the usual fashion.

Figure 7:
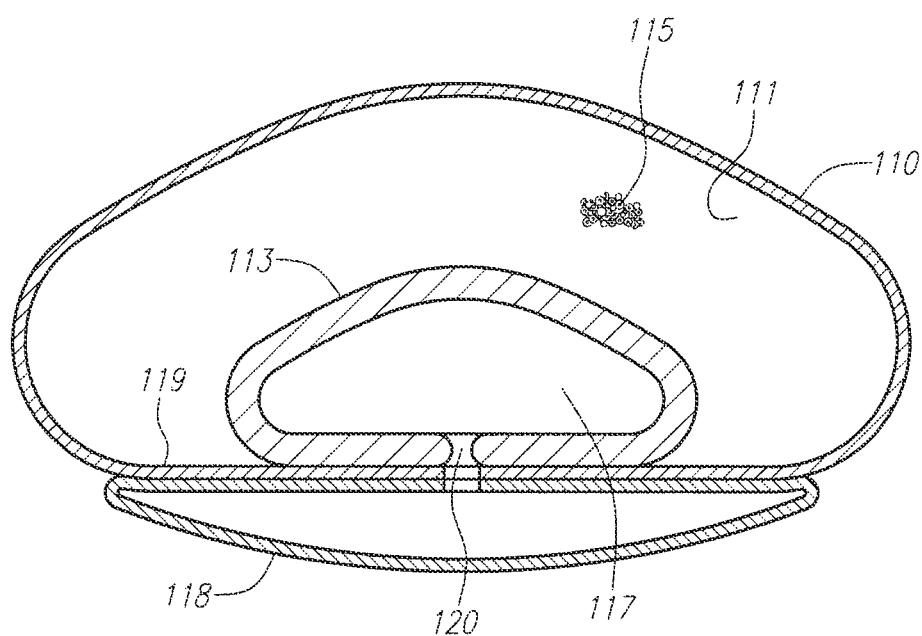
FIG. 7 is a vertical cross-section of the invention showing the implant, the shell, the slurry filler compartment, the reservoir and the limiting membrane region.

FIG. 6 shows a cross-section of the inventive implant in a general form. A shell 110 serves as the exterior surface of the implant. The shell 110 may be of a single material, or may be made of multiple layers (see, e.g., the embodiment of FIG. 7). Within the shell 110 is a slurry filler compartment 111 which is adapted to receive slurry filler 115 (shown enlarged in FIG. 9), or if the implant has been filled, will contain the slurry filler. The drawing of FIG. 6 and FIG. 7 only show a portion of the slurry filler for illustrative purposes, it being appreciated that the slurry filler would typically occupy the entirety of the slurry filler compartment 111 when fully filled. The slurry filler compartment 111 may either be an additional structure or may be the space defined by other structures such as the inside of the shell 110 and outside of the fluid compartment 113. A fluid compartment 113 is in pressure transmissive contact with the slurry filler. The fluid compartment 113 is deformable from a neutral profile under pressure from the slurry filler and which recoils to the neutral profile when not under pressure. The fluid compartment 113 contains an interior fluid space 117 adapted to hold, or if filled, holds the fluid. A reservoir 118 is disposed preferably external to the shell. The reservoir 118 and fluid space 117 are fluidically coupled such as by a port or tunnel 120. A limiting membrane region 119 is generally disposed between the fluid compartment 113 and the reservoir 118. While the limiting membrane region 119 may be a separate additional structure, such as an annular disk having a hole centered with the port 120, the limiting membrane region 119 may be formed from the materials located there, e.g., the shell 110, reservoir 118 and fluid compartment 113, all where they join at the back of the implant. The region 119 serves to provide sufficient structural rigidity so that the pressure transmission from the slurry filler can be effectively transmitted to the fluid compartment 113 and in turn be relieved by expansion of the reservoir 118 by fluid passing from the fluid space 117 through the port 120. The comments made here regarding the general embodiment depicted in FIG. 6 also apply to the more detailed embodiment described, below.

Figure 8:
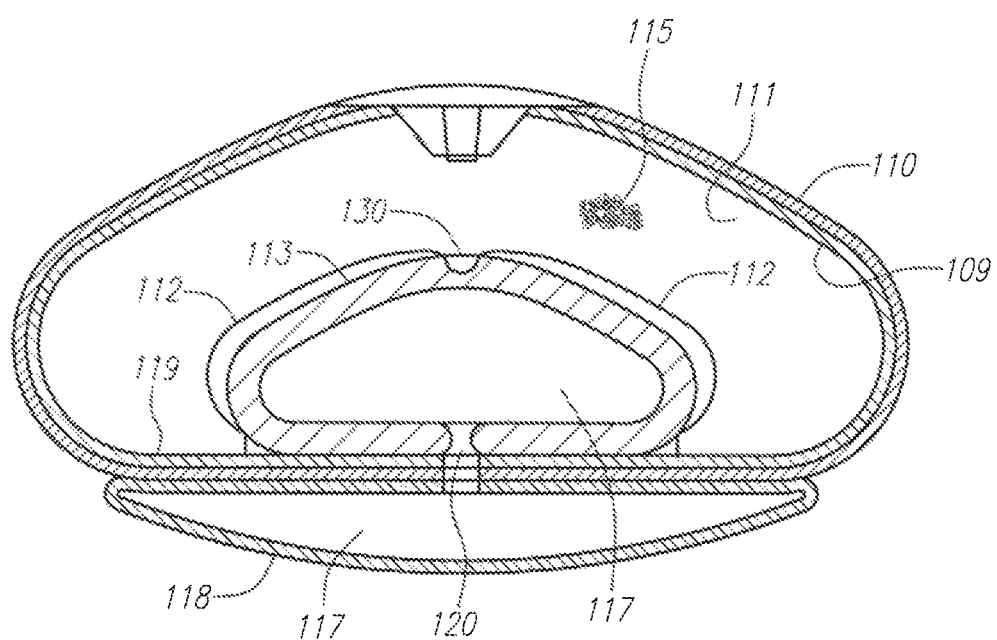
FIG. 8 is a vertical cross-section of one more detailed aspect of the invention showing the sessile nature of the normal saline-filled buttress and its attachment to the thick internal base of the implant as well as a side view of its relationship with the slurry-containing compartment and the lens-like normal saline-containing reservoir.

FIG. 8 is a vertical cross section of the invention in a particular embodiment adapted for ease of manufacture. The implant shell 110 consists of a compliant silicone elastomer shell plus a laminated low bleed layer 109 adherent to the inner surface. The shell defines volume 111 which is occupied by slurry filler 115 (see also FIG. 9) and buttress or fluid compartment 113. The buttress is adhesively attached to a thick skirt 119 which is in turn adhesively attached at the center of the internal base of the shell 110, their central axes all coinciding with the thick limiting membrane which is interposed. Port 120 is a short tunnel connecting buttress 113 and reservoir 118 and passing through thick membrane 119. The reservoir 118 is lens-like in configuration and is delimited at its periphery by adhesive affixation to the thick skirt membrane 119.

The fluid in fluid space 117 is a biocompatible fluid, preferably 0.9% NaCl buffered to pH 7.0 and is also a component of the slurry filler 115. The fluid is located in both the fluid space 117 of the buttress 113 and reservoir 118. The fluid is preferably introduced into the volume 111 of slurry filler compartment through a fillport and then into the buttress 113 via syringe and hollow needle puncture. A measured volume is injected and the needle withdrawn. All air must be eliminated from this compartment. The needle puncture site on the buttress then is sealed with a liquid silicone patch 130 and later cured.

Figure 9:
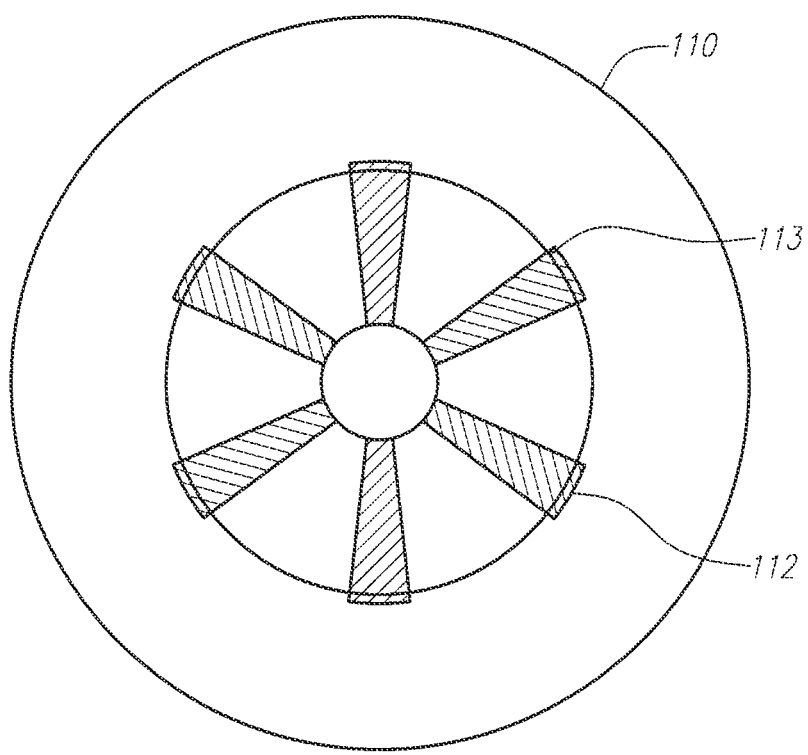
FIG. 9 is a transparent top view of the invention illustrating surface detail of the buttress and slurry fill port.

FIG. 9 illustrates the buttress 113 relationship to other structural components in a top "transparent view" of the implant with buttress 113 surface detail and ghosted slurry fillport at the apex of the implant. The structures in FIG. 8 help clarify the terminology used herein. The term that buttress 113 refers to is to be understood to be the fluid compartment 113, which has the attributes described previously, namely that it is a structure deformable from a neutral profile under pressure from the slurry filler and which recoils to the neutral profile when not under pressure. The buttress structural member 112 in FIG. 9 adhered to the exterior of the fluid compartment or buttress 113 is meant to refer to buttress in the narrower sense of an additional structure provided to steady or support another structure. The buttress structural member 112 may be provided on the exterior of the fluid compartment or buttress 113 (as shown in FIG. 9) or may be internal to the fluid compartment or buttress 113.

Figure 10:
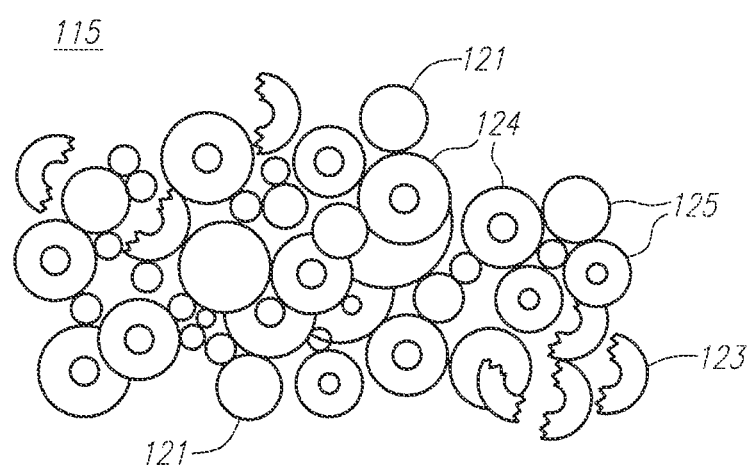
FIG. 10 is an illustration of particulate components of the slurry greatly magnified including spatial relationships and interference with one another.
Figure 11:
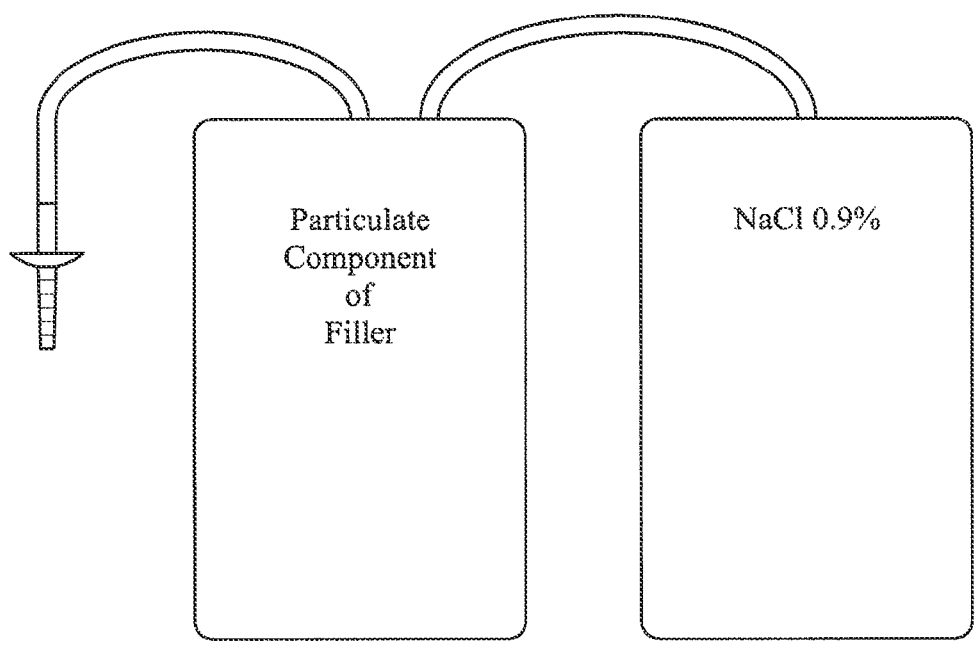
FIG. 11 is an illustration of a fill kit including attached bags, tubing, valves and solid and liquid components of slurry filler.

FIG. 10 illustrates origins of frictional interference of particulates in the slurry filler 15. Slurry filler 115 is comprised of a mixture of buffered 0.9% NaCl and medical glass spheres 121 or micro-toroids 122 or biocompatible polymer structural equivalents in prodigious numbers. The globules or toroids may all be comprised of the same diameter or may be a mixture of diameters satisfying "closest packing" specifications. The solid component is essentially a powder of globules and toroids in the range ideally between 500 microns-2.0 mm. Amorphous "frit" 123 selected from the same materials serves to add friction. Such "closest packing" criteria allow for optimal friction. Other physical features of such an admixture optimized for performance include etched 124 and/or metal plated particulates 125. Operating also in the slurry are surface tension and electrostatic forces. The net viscosity is a function of all such factors operating together. Metal silver plating of particulates will confer antibiotic/bacteriostatic properties to the slurry.

Overall performance of the implant here will be defined as its ability to simulate a gel-filled implant. If shell 110 is indented, the slurry filler 115 is caused to flow diffusely away from the area of deformation and toward the buttress and, in turn fluid 117. Fluid 117 is caused to move via tube 120 into reservoir 118. The lens-like reservoir partially fills and assumes a thicker lens-like configuration. The pulsion on the implant, by virtue of the slurry having a toothpaste-like consistency, modulates the propagation of pressure waves through it and along with the displaced saline 117 in the volume being transferred from the buttress 113 to the reservoir 118, achieves the modulation of applied external pressure and simulates the performance of a gel.

Upon release of the pressure on the implant, there is a reversal of the aforementioned sequence of events: Buttress 113 is constructed so as to maximize its recoil back to its original shape and in doing so "aspirates" fluid 117 and resumes its former volume, thus causing the whole implant profile and volume to be reestablished. The lens-like reservoir 118 has the capacity to distribute fluid over a wide area underneath the implant so that its volume expansion and contraction are hardly noticeable. Importantly, repeated pulsed stretching of scar tissue surrounding the implant during initial wound healing will result in an appropriately enlarged scar envelope around the implant. As external pressure is relieved, and equilibrium reestablished, the patient's tissues again resume their former appearance.

The choice of materials may be broadly chosen as to those known to people skilled in the art. For example, the spring may be made of metal, such as spring metal or stainless steel, of otherwise consistent with the goals and objects of the inventions. Non-metallic materials, such as polymers, may be utilized to overmold metallic springs. Materials which will contact the user of the implant should be biocompatible.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

I claim:

1. An implantable prosthesis comprising:
   a shell, the shell including an opening,
   an urchin buttress, the urchin buttress being disposed within the shell, the urchin buttress being attached to the shell via a flange oriented toward the center of the implant adjacent the opening, the flange and the shell forming a fluidic seal, thereby forming a compartment interior to the shell and exterior to the urchin buttress, the compartment adapted to contain a filler,
   a reservoir, the reservoir being disposed external to the shell and in fluid communication with the interior of the urchin buttress, and
   at least one fill port.

2. The implantable prosthesis of claim 1 further including a basilar membrane between the shell and the reservoir.

3. The implantable prosthesis of claim 1 further including a ridge disposed on the flange of the urchin buttress.

4. The implantable prosthesis of claim 1 wherein the urchin buttress includes an internal guide surface.

5. The implantable prosthesis of claim 1 wherein the at least one fill port includes a sealing access port.

6. The implantable prosthesis of claim 1 further including a sealing flange for the urchin buttress.

7. The implantable prosthesis of claim 1 wherein the shell comprises silicon elastomer.

8. The implantable prosthesis of claim 1 wherein the cup-shaped buttress is semi-spherical.

9. The implantable prosthesis of claim 1 wherein the fluid compartment includes a modulating buttress.

10. The implantable prosthesis of claim 1 wherein the filler is normal saline.

11. The implantable prosthesis of claim 1 wherein the filler is a slurry.

12. The implantable prosthesis of claim 1 wherein the urchin buttress further includes one or more ribs.

13. The implantable prosthesis of claim 1 further including a spring disposed within the urchin buttress.

14. The implantable prosthesis of claim 13 wherein the spring is a coil spring.

15. The implantable prosthesis of claim 13 further including a curb adjacent the spring.

16. The implantable prosthesis of claim 1 wherein at least two fill ports are provided.

17. The implantable prosthesis of claim 1 wherein a slurry fill port is disposed on the shell.

18. The implantable prosthesis of claim 1 wherein a saline fill port is disposed on the shell.

19. The implantable prosthesis of claim 1 wherein the urchin buttress includes a screen above a fill port.

20. The implantable prosthesis of claim 1 wherein the prosthesis is a mammary prosthesis.

21. A kit comprising the implant of claim 1 and a cannula adapted for coupling to a fluid source.

22. An implantable prosthesis comprising:
a shell, the shell having an exterior surface and an interior surface, and including an opening,
a buttress, the buttress having an exterior surface and an interior surface, the buttress being disposed within the shell, the buttress being attached to the shell via a flange, the flange and the shell forming a fluidic seal, thereby forming a first fluidic compartment interior to the shell and exterior to the buttress, the first fluidic compartment adapted to contain a filler, the interior of the buttress defining a second fluidic compartment,
a deformation resilient, member adjacent the buttress,
a reservoir, the reservoir being disposed adjacent the shell and in fluid communication with the second fluidic compartment, and
at least one fill port.

23. The implantable prosthesis of claim 22 wherein the buttress is an urchin buttress.

24. The implantable prosthesis of claim 22 wherein the buttress is a limpet buttress.

25. The implantable prosthesis of claim 22 wherein the deformation resilient member adjacent the buttress is a spring.

26. The implantable prosthesis of claim 22 wherein the deformation member adjacent the buttress is a rib.

27. The implantable prosthesis of claim 22 further including a fill port through the shell.

28. The implantable prosthesis of claim 27 wherein the fill port through the shell is a slurry fill port.

29. An implantable mammary prosthesis comprising:
a shell,
a first filler compartment interior to the shell adapted to contain a first filler,
a hollow fluid compartment, the fluid compartment being deformable from a neutral profile under pressure from the first filler and which recoils to the neutral profile when not under pressure, the hollow fluid compartment being disposed within the first filler compartment, the hollow fluid compartment and shell forming a fluidic seal, and
a reservoir, the reservoir being disposed external to the shell, the reservoir and fluid compartment being fluidically coupled by a port.

30. The implantable mammary prosthesis of claim 29 wherein the first filler is a slurry.

* * * * *